United States Patent
McCray, Jr. et al.

(10) Patent No.: US 9,272,016 B2
(45) Date of Patent: Mar. 1, 2016

(54) METHODS TO ENHANCE RNAI OLIGONUCLEOTIDE DELIVERY TO RESPIRATORY EPITHELIAL CELLS

(71) Applicant: University of Iowa Research Foundation, Iowa City, IA (US)

(72) Inventors: Paul B. McCray, Jr., Iowa City, IA (US); Beverly L. Davidson, Iowa City, IA (US); Sateesh Krishnamurthy, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 118 days.

(21) Appl. No.: 13/828,488

(22) Filed: Mar. 14, 2013

(65) Prior Publication Data

US 2013/0281372 A1    Oct. 24, 2013

Related U.S. Application Data

(60) Provisional application No. 61/636,406, filed on Apr. 20, 2012.

(51) Int. Cl.
| | |
|---|---|
| *A61K 48/00* | (2006.01) |
| *A61K 38/18* | (2006.01) |
| *A61K 31/713* | (2006.01) |
| *A61K 31/7064* | (2006.01) |
| *A61K 31/352* | (2006.01) |
| *A61K 31/519* | (2006.01) |
| *A61K 31/5377* | (2006.01) |
| *A61K 31/7105* | (2006.01) |

(52) U.S. Cl.
CPC ........... *A61K 38/1808* (2013.01); *A61K 31/352* (2013.01); *A61K 31/519* (2013.01); *A61K 31/5377* (2013.01); *A61K 31/7064* (2013.01); *A61K 31/713* (2013.01); *A61K 31/7105* (2013.01)

(58) Field of Classification Search
None
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 6,855,549 B1 | 2/2005 | McCray, Jr. et al. |
| 8,084,599 B2 | 12/2011 | Rossi et al. |
| 2005/0032723 A1* | 2/2005 | Renzi et al. ............ 514/44 |
| 2011/0268722 A1* | 11/2011 | Siegelin et al. ......... 424/130.1 |

OTHER PUBLICATIONS

Xu et al. Antiviral Research 61 (2004) 195-206.*
Behlke, "Chemical modification of siRNAs for in vivo use", Oligonucleotides, 18(4), 305-319 (2008).
Bitko et al., "Inhibition of respiratory viruses by nasally administered siRNA", Nat Med, 11(1), 50-55 (2005).
Davidson et al., "Current prospects for RNA interference-based therapies", Nat Rev Genet, 12(5), 329-340 (2011).
Devincenzo et al., "A randomized, double-blind, placebo-controlled study of an RNAi-based therapy directed against respiratory syncytial virus", Proc Natl Acad Sci, 107(19), 8800-8805 (2010).
Judge et al., "Sequence-dependent stimulation of the mammalian innate immune response by synthetic siRNA", Nat Biotechnol, 23(4), 457-462 (2005).
Karp et al., "An in vitro model of differentiated human airway epithelia. Mehtods for establishing primary cultures", Methods Mol Biol, 188, 115-137 (2002).
Kim et al., "Synthetic dsRNA dicer substrates enhance RNAi potency and efficacy", Nat Biotechnol, 23(2), 222-226 (2005).
Kleinman et al., "Sequence- and target-independent angiogenesis suppression by siRNA via TLR3", Nature, 452, 591-597 (2008).
Krishnamurthy et al., "Manipulation of airway epithelia to improve siRNA delivery and RNAi efficacy", presented at American Society of Gene & Cell Therapy 15th Annual Meeting, Abstract No. 350787, 2 pages, (May 2012).
Krishnamurthy et al., "Manipulation of Cell Physiology Enables Gene Silencing in Well-differentiated Airway Epithelia", Molecular Therapy-Nucleic Acids 1, e41, 1-10 (2012).
Lamb et al., "The connectivity map: Using gene-expression signatures to connect small molecules, genes, and disease", Science, 313, 1929-1935 (2006).
Moschos et al., "Uptake, efficacy, and systemic distribution of naked, inhaled short interfering RNA (siRNA) and locked nucleic acid (LNA) antisense", Mol Ther, 19(12), 2163-2168 (2011).
Oakland et al., "Advances in cell and gene-based therapies for cystic fibrosis lung disease", Mol Ther, vol. 20 (6), 1108-1115, Feb. 28, 2012, doi: 10.1038/mt.202.32.[Epub ahead of print]PMID: 22371844.
Rose et al., "Functional polarity is introduced by Dicer processing of short substrate RNAs", Nucleic Acids Res, 33 (13), 4140-4156 (2005).
Ross et al., "Transcriptional profiling of mucociliary differentiation in human airway epithelial cells", Am J Respir Cell Mol Biol, 37(2), 169-185 (2007).
Sinn et al., "Viscoelastic Gel Formulations Enhance Airway Epithelial Gene Transfer with Viral Vectors", Am J Respir Cell Mol Biol, 32(5), 404-410 (2005).
Zhang et al., "Inhibition of respiratory syncytial virus infection with intranasal siRNA nanoparticles targeting the viral NS1 gene", Nat Med, 11(1), 56-62 (2005).

* cited by examiner

*Primary Examiner* — Kimberly Chong
(74) *Attorney, Agent, or Firm* — Viksnins Harris & Padys PLLP

(57) ABSTRACT

The present invention relates to methods of reducing a level of a target mRNA in a well-differentiated airway epithelial cell by contacting the cell with a sensitizing agent followed by contacting the cell with a therapeutic RNAi agent.

15 Claims, 12 Drawing Sheets

US 9,272,016 B2

METHODS TO ENHANCE RNAI OLIGONUCLEOTIDE DELIVERY TO RESPIRATORY EPITHELIAL CELLS

PRIORITY OF INVENTION

Figure 1:
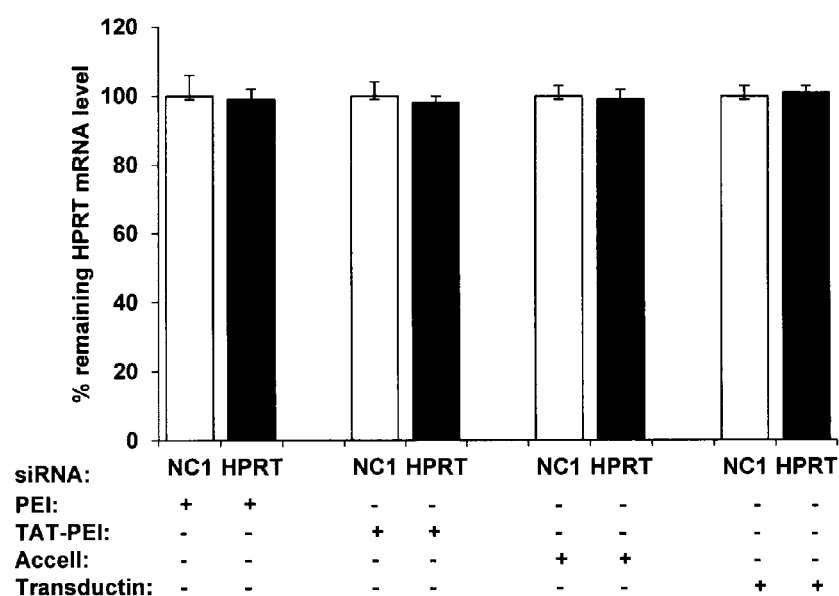
Figure 1:

This application claims priority to U.S. Provisional Application No. 61/636,406 that was filed on Apr. 20, 2012. The entire content of this provisional application is hereby incorporated herein by reference.

STATEMENT REGARDING FEDERALLY SPONSORED RESEARCH

This invention was made with government support under grant number PO1 HL-51670 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Mar. 13, 2013, is named 17023.121US1_SL.txt and is 6,874 bytes in size.

BACKGROUND OF THE INVENTION

Small-interfering RNA (siRNA)-mediated silencing of genes offers a novel approach for disease treatment. Direct delivery of siRNA to respiratory epithelia is potentially advantageous for many respiratory infections and for chronic diseases like cystic fibrosis where airway epithelial cells are prominent sites of production and release of pro-inflammatory cytokines such as IL-8 and others (Davidson B L, McCray P B, Jr. Current prospects for RNA interference-based therapies. Nat Rev Genet 2011; 12(5):329-340). Topical delivery avoids hepatic clearance and non-specific accumulation associated with the systemic route and allows for local accumulation within the target organ. But due to its high molecular weight and polyanionic nature, siRNAs do not cross the epithelial cell membrane freely. In addition, the intra pulmonary physical barriers such as mucus to overcome before encountering the problems with cell entry (Oakland M, Sinn P L, McCray P B Jr. Advances in cell and gene-based therapies for cystic fibrosis lung disease. Mol Ther. 2012 Feb. 28. doi: 10.1038/mt.2012.32. [Epub ahead of print] PMID: 22371844). Thus, efficient delivery of siRNA to the airways has been challenging due to significant intracellular and extracellular barriers.

Non-viral siRNA delivery is an attractive and potentially safer alternative to virus-based delivery systems. A number of studies report successful delivery of naked siRNA to airways, especially for counteracting viral infections (Zhang W et al., Inhibition of respiratory syncytial virus infection with intranasal siRNA nanoparticles targeting the viral NS1 gene. Nat Med 2005; 11(1):56-62; Bitko V et al., Inhibition of respiratory viruses by nasally administered siRNA. Nat Med 2005; 11(1):50-55). However, recent reports also show that siRNAs delivered intranasally or intratracheally, without delivery enhancement, may not target to lung cells and thus do not cause RNA interference (Moschos S A et al., Uptake, efficacy, and systemic distribution of naked, inhaled short interfering RNA (siRNA) and locked nucleic acid (LNA) antisense. Mol Ther 2011; 19(12):2163-2168). Furthermore, off target immunostimulatory effects of early siRNA constructs likely clouded some studies (Judge A D et al., Sequence-dependent stimulation of the mammalian innate immune response by synthetic siRNA. Nat Biotechnol 2005; 23(4):457-462; DeVincenzo J et al., A randomized, double-blind, placebo-controlled study of an RNAi-based therapy directed against respiratory syncytial virus. Proc Natl Acad Sci USA 2010; 107(19):8800-8805; Kleinman M E et al., Sequence- and target-independent angiogenesis suppression by siRNA via TLR3. Nature 2008; 452 (7187):591-597). Added to these disappointing results, the delivery and efficacy of siRNA in combination with various non-viral reagents in respiratory epithelia has not been extensively investigated.

Accordingly, a more effective, simple-to-administer, and efficient treatment for airway epithelial disease is needed.

SUMMARY OF THE INVENTION

In certain embodiments, the present invention provides a method of reducing a level of a target mRNA in a well-differentiated airway epithelial cell comprising contacting the cell with a sensitizing agent followed by contacting the cell with a therapeutic RNAi agent, wherein the mRNA level of the target mRNA is reduced by at least 1% as compared to a control cell that has not been contacted with the sensitizing compound. As used herein, the term "well-differentiated" cells have fully differentiated and form a pseudostratified epithelium with the diversity of cells represented in the human conducting airways (ciliated cells, goblet cells, non-ciliated cells, basal cells) and "poorly-differentiated" cells to signify cells that have not reached this differentiated state of maturation and do not form an epithelium representative of the in vivo airways. As used herein an "RNAi molecule" is an RNA molecule that functions in RNA interference (e.g., siRNA, shRNA or DsiRNA). In certain embodiments, the mRNA level is reduced by at least about 1%, 5%, 10%, 20, 30%, 40%, 50%, 60%, 70%, 80%, 90% 95%, or 99%. In certain embodiments, the well differentiated cells are more than five days old. In certain embodiments, the cell is contacted on its mucosal surface. In certain embodiments, the airway epithelial cell is a lung cell, a nasal cell, a tracheal cell, a bronchial cell, a bronchiolar or alveolar epithelial cell.

In certain embodiments, the sensitizing agent is a small molecule PI3K inhibitor. In certain embodiments, the sensitizing compound is EGF. In certain embodiments, the sensitizing agent is LY-294002 (2-morpholin-4-yl-8-phenyl-chromen-4-one), wortmannin or triciribine.

In certain embodiments, the RNAi molecule is an siRNA, an miRNA, a microRNA mimic, and anti-Mir and/or an antisense oligonucleotide. In certain embodiments, the present invention provides a method of treating a subject having an airway epithelial disease comprising administering to the subject an effective amount of a sensitizing agent and an effective amount of a therapeutic agent to alleviate the symptoms of the airway epithelial disease by inducing a therapeutic effect. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effects can be measured quantitatively by a physician or qualitatively by a patient afflicted with the disease state targeted by the therapeutic agent.

In certain embodiments, the sensitizing agent and/or therapeutic agent is administered orally, by inhalation, by aerosol, dry powder, bronchoscopic instillation, or intra-airway (tracheal or bronchial) aerosol. In certain embodiments, the therapeutic RNAi agent is present within a pharmaceutical composition. In certain embodiments, the airway epithelial disease is cystic fibrosis. In certain embodiments, the subject is a mammal, such as a human. In certain embodiments the symptoms are reduced by at least 1%, 5%, 10%, 20, 30%, 40%, 50%, 60%, 70%, 80%, 90% 95%, or 99%. In certain embodiments, the sensitizing agent is EGF. In certain embodiments, the sensitizing agent is a small molecule PI3K inhibitor, such as LY-294002, wortmannin and/or triciribine.

In certain embodiments, the present invention provides a kit for reducing a level of a target mRNA in a well-differentiated PAE cell comprising (a) a sensitizing agent, (b) a therapeutic RNAi molecule, and (c) instructions for contacting the cell with the sensitizing compound and the RNAi molecule to reduce the mRNA level of the target mRNA by at least 1% as compared to a control cell that has not been contacted with the sensitizing compound.

In certain embodiments, the epithelial cell, such as an airway epithelial cell (e.g., a lung cell, a nasal cell, a tracheal cell, a bronchial cell, a bronchiolar or alveolar epithelial cell). In certain embodiments, the airway epithelial cells are present in a mammal.

BRIEF DESCRIPTION OF DRAWINGS AND TABLE

FIG. 1. siRNA delivery has no silencing effect in well differentiated PAE (primary pig airway epithelia) HAE is primary human airway epithelia cultures. (a) Well differentiated PAE cultures were transfected with HPRT or NC1 siRNA (250 nM) using either PEI or TAT-PEI, Accell siRNA or Transductin at the indicated concentrations. The cells were harvested for RNA after 24 h, and the RNA was reverse transcribed into cDNA, which was then quantified by qPCR. All the mRNA levels normalized to those of the NC1 samples (100%). Mean levels (±s.d.) were calculated from three replicate transfections. (b-c) Confocal imaging of epithelia 2 h after transfection with DIG-HPRT siRNA complexed with transductin (b) or without any transfection reagent (c).

Figure 2:
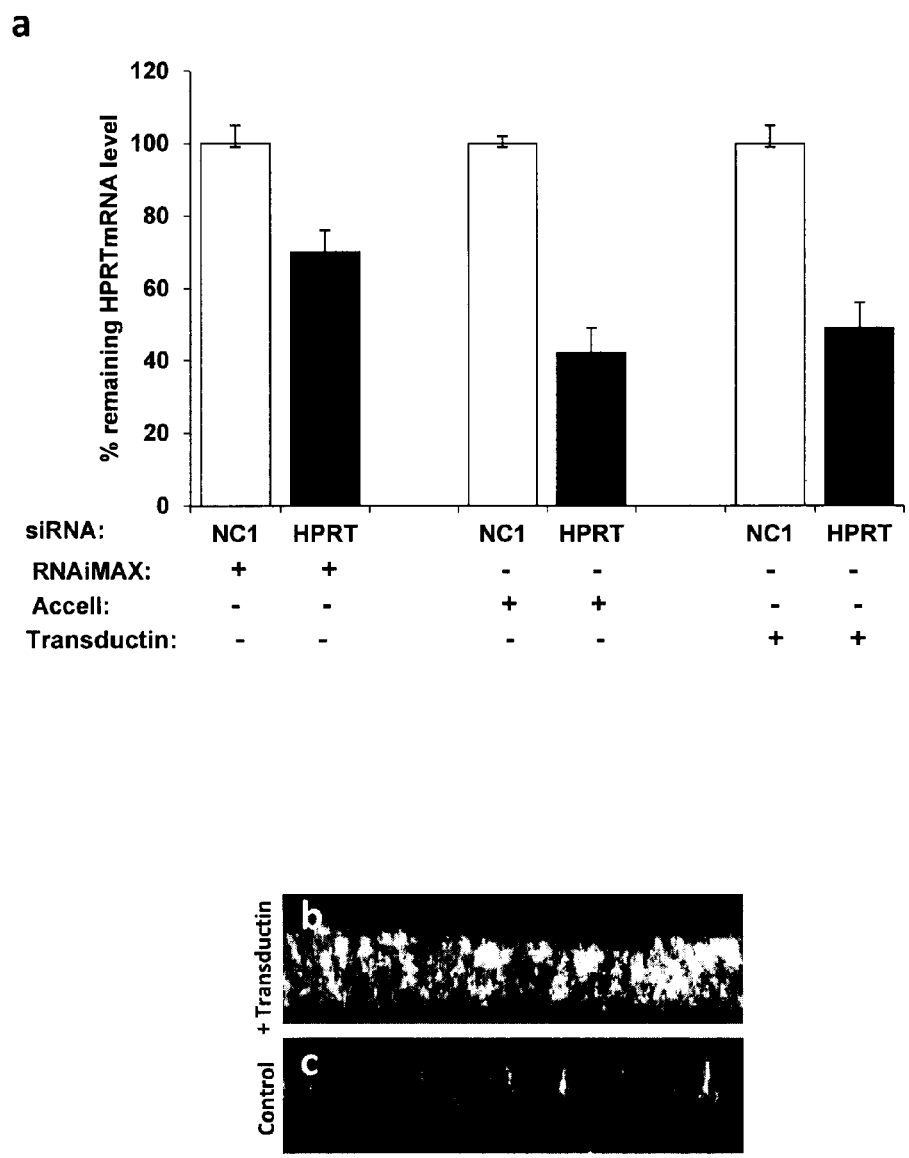

FIG. 2. siRNAs effectively silence targets in poorly differentiated PAE cultures. (a) Poorly differentiated cultures, 2-day post-seeding, were transfected with 250 nM of siRNA against HPRT with the use of RNAiMAX, Accell siRNA, or Transductin at the indicated concentrations and then processed (RNA isolation, cDNA synthesis and qPCR) 24 h later. The percentages of remaining mRNA levels in samples were graphed in comparison with those of negative control (NC1), which was set at 100%. Mean levels (±s.d.) were calculated from three replicate transfections. (b-c) Confocal imaging of cells 2 h after transfection with DIG-HPRT siRNA complexed with Transductin (b) or without any transfection reagent (c).

Figure 3:
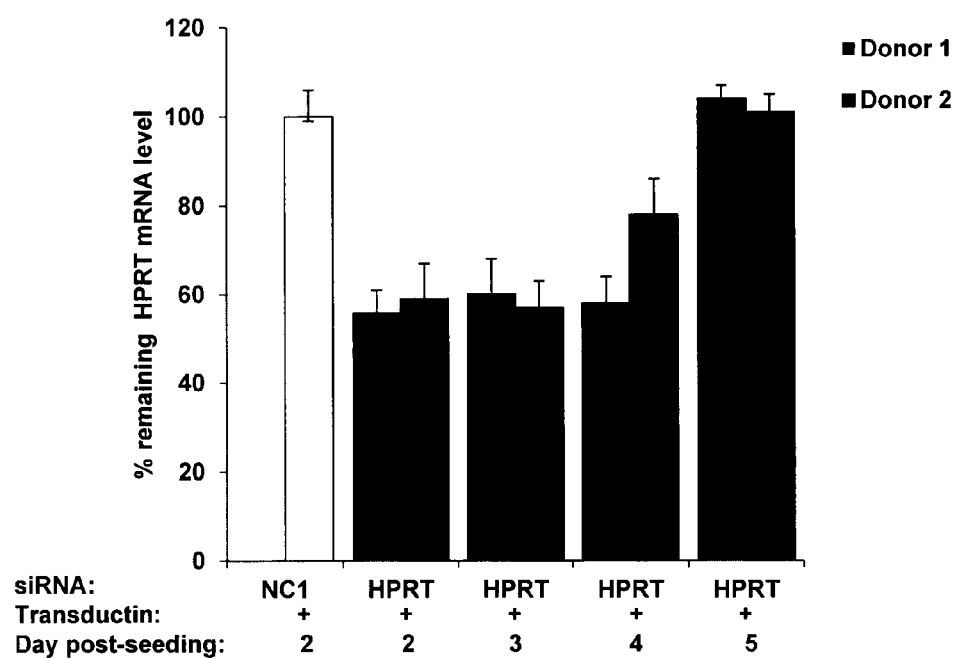
Figure 3:
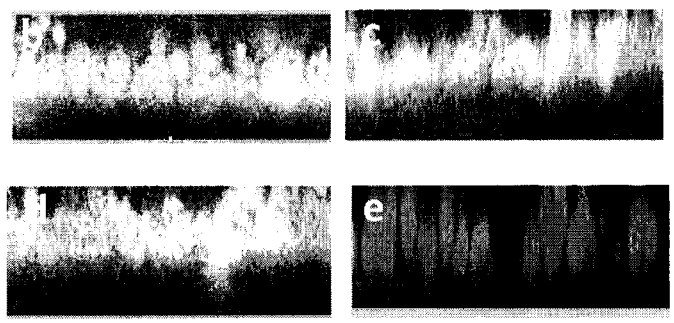

FIG. 3. Effective silencing of targets is seen only in pig airway cells that are less than 5-days old (a) Pig airway epithelia from 2 donors that were 2 to 5 days old (2 D to 5 D) were transfected with siRNA against HPRT (250 nM) using Transductin. The cells were processed for RNA isolation and cDNA synthesis 24 h later and then subjected to qPCR for quantification of HPRT mRNA. The bars for HPRT samples denote the mRNA levels remaining normalized to the NC1 samples (100%). Mean levels (±s.d.) were calculated from three replicate transfections. (b-e) Confocal imaging of 2 (b), 3(c), 4(d) and 5(e) days old cells after transfection of each with DIG-HPRT siRNA and then staining 2 h later for antibody to DIG followed by fluorescent dye tagged secondary antibody.

Figure 4:
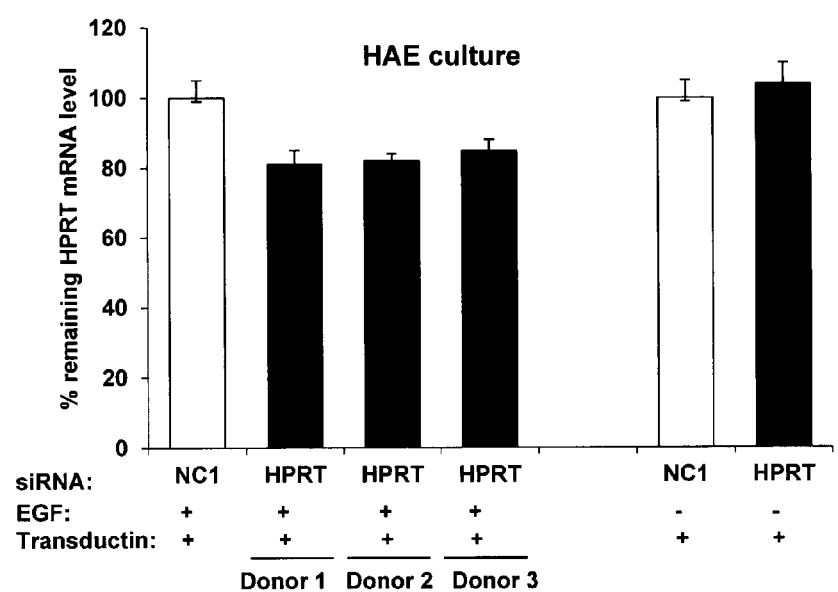

FIG. 4. EGF treatment of cells prior to siRNA delivery enhances entry and cause modest silencing. Well-differentiated airway cells from 3 donors were treated apically with EGF at a concentration of 100 µg/ml for 15 min before transfecting them with siRNA against HPRT at a concentration of 250 nM. Twenty four hours later, the cells were processed for RNA isolation, cDNA synthesis and qPCR quantification of HPRT mRNA. NC1 mRNA levels, treated or untreated with EGF were set at 100% and used for comparison with HPRT treated samples. Mean levels (±s.d.) were calculated from three replicate transfections.

Figure 5:
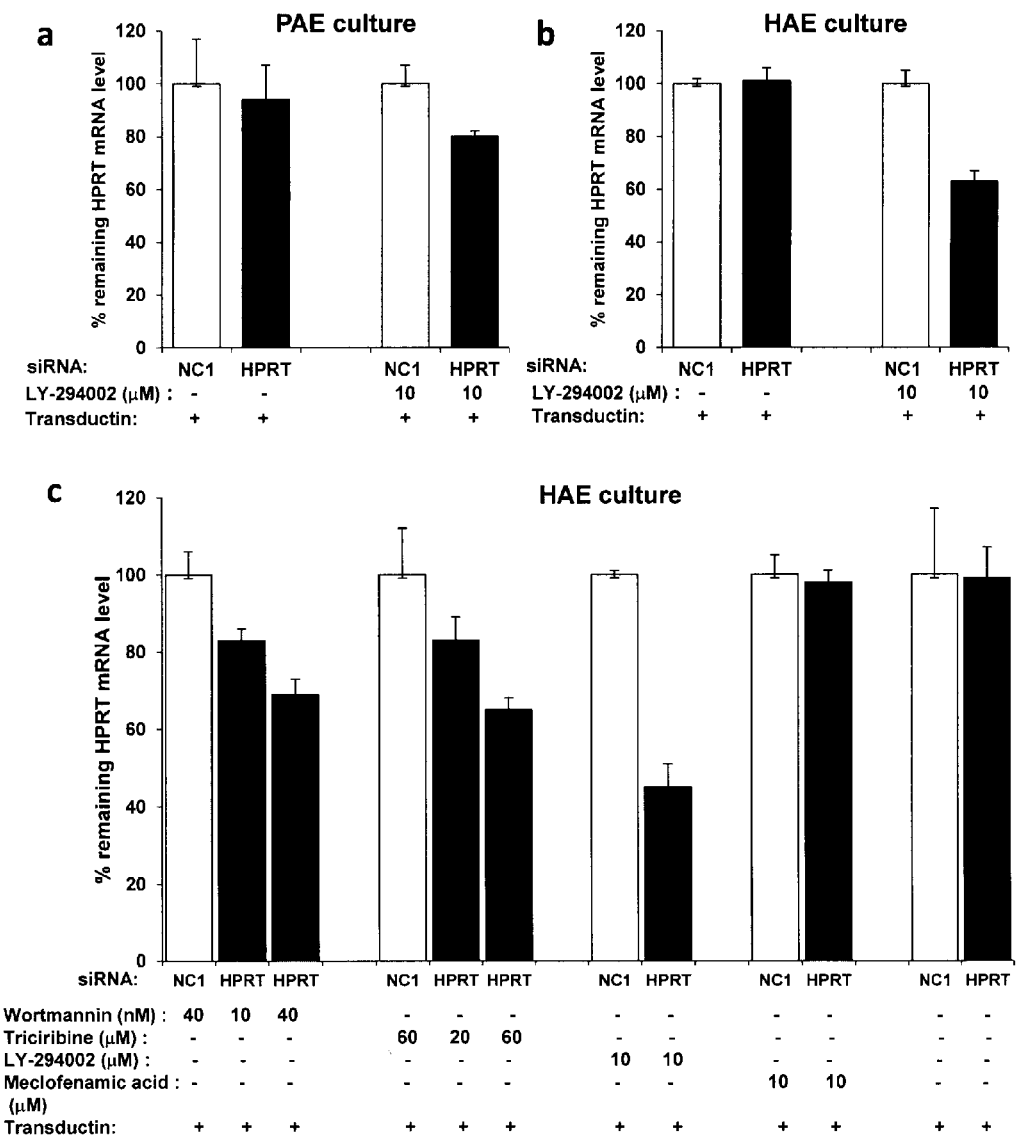

FIG. 5. Small molecule treatments of cells prior to siRNA delivery cause effective silencing of targets. (a-b) Human airway epithelia (a) and pig airway epithelia (b) were treated apically with LY-294002 at a concentration of 10 µM for 6 h or untreated before transfecting them with respective siRNAs against HPRT. (c) Human airway cells were either untreated or treated with other small molecule PI3K inhibitors, wortmannin, and triciribine, each at two different concentrations as a control meclofenamic acid, a drug with a positive correlation in CMAP analysis were added before transfection with siRNA against HPRT. mRNA levels were assessed by real time PCR and normalized to NC1. Mean levels (±s.d.) were calculated from three replicate transfections.

Figure 6:
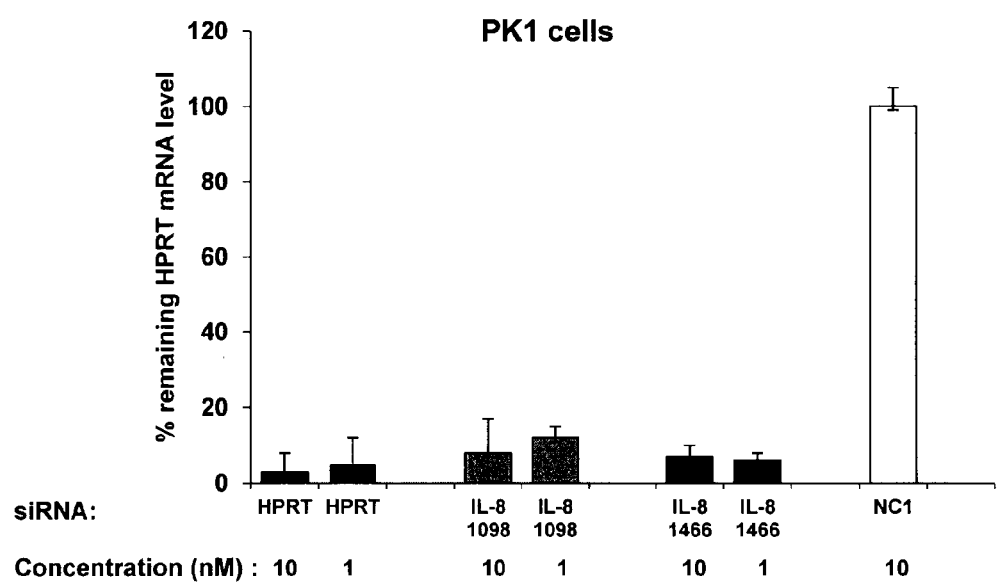

FIG. 6. Dicer-substrate siRNA silence gene expression in PK1 cells. PK1 cells were reverse transfected with the indicated concentration of siRNA against HPRT, IL-8 (1098), IL-8 (1466) or with the negative control siRNA, NC, all with the use of the lipid transfection reagent, RNAiMAX. Twenty four hours later the cellular RNA was isolated, reversed transcribed and subjected to qPCR using the respective gene specific primers and probes. The NC1 samples were quantified for both HPRT and IL-8 mRNA levels. The remaining mRNA levels of all the samples are displayed in comparison with NC1, which was set at 100%. Mean levels (±s.d.) were calculated from three replicate transfections.

Figure 7:
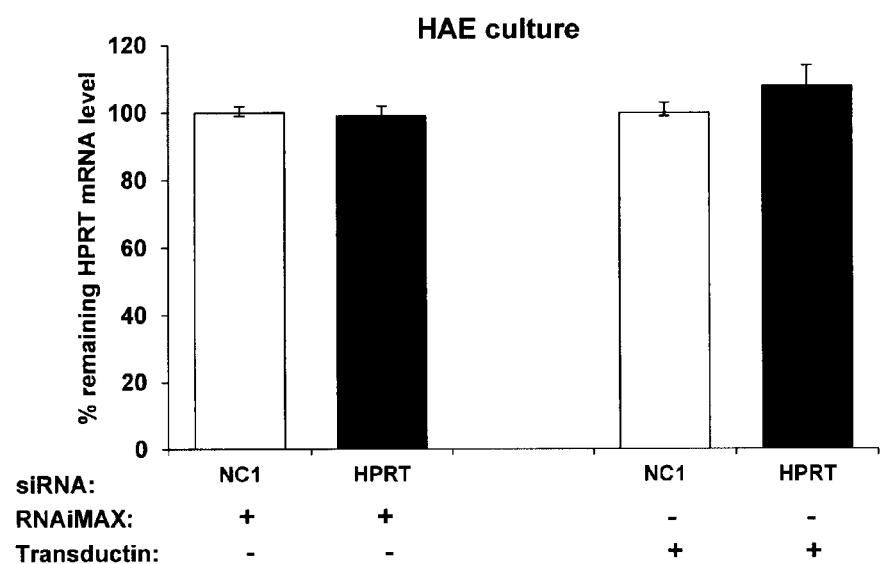

FIG. 7. siRNA delivery has no silencing effect in well-differentiated HAE cultures (primary human airway epithelia cultures). HAE cultures were transfected with HPRT siRNA using RNAiMAX or Transductin and subjected to qPCR after RNA isolation and cDNA synthesis. HPRT mRNA levels of the samples are compared to that of the negative control (100%). Mean levels (±s.d.) were calculated from three replicate transfections.

Figure 8:
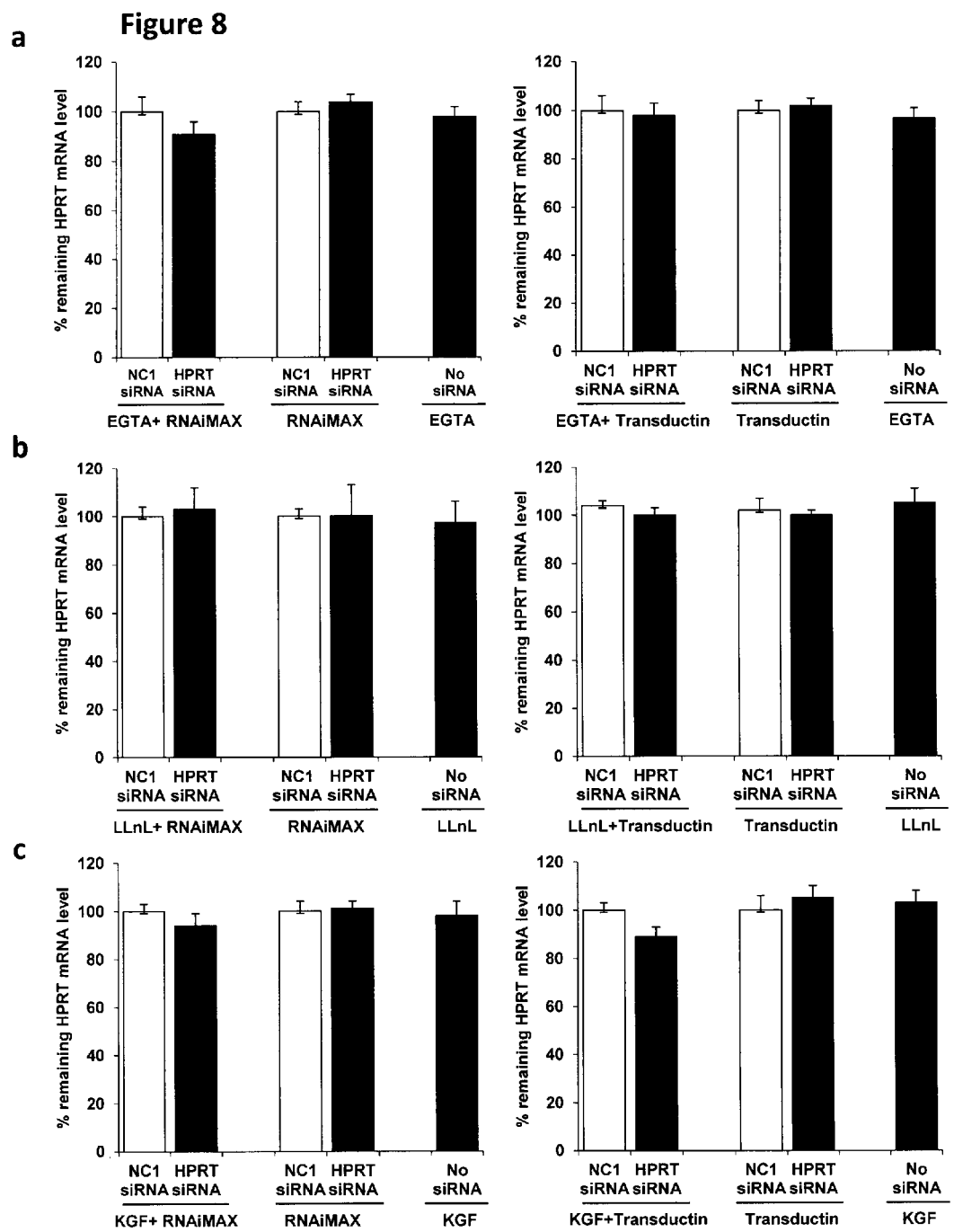

FIG. 8. siRNA delivery has no silencing effect in well differentiated PAE cultures treated with EGTA, LLnL or KGF. (a-c) Pig airway epithelia were either untreated or treated apically with EGTA, LLnL, or KGF under the conditions described in Materials and Methods, before transfection with 250 nM HPRT siRNA using either RNAiMAX or Transductin. The cells were processed for qPCR and mRNA quantified. Bars represent HPRT mRNA levels. HPRT mRNA levels in NC1 samples were set at 100%. Mean levels (±s.d.) were calculated from three replicate transfections.

Figure 9:
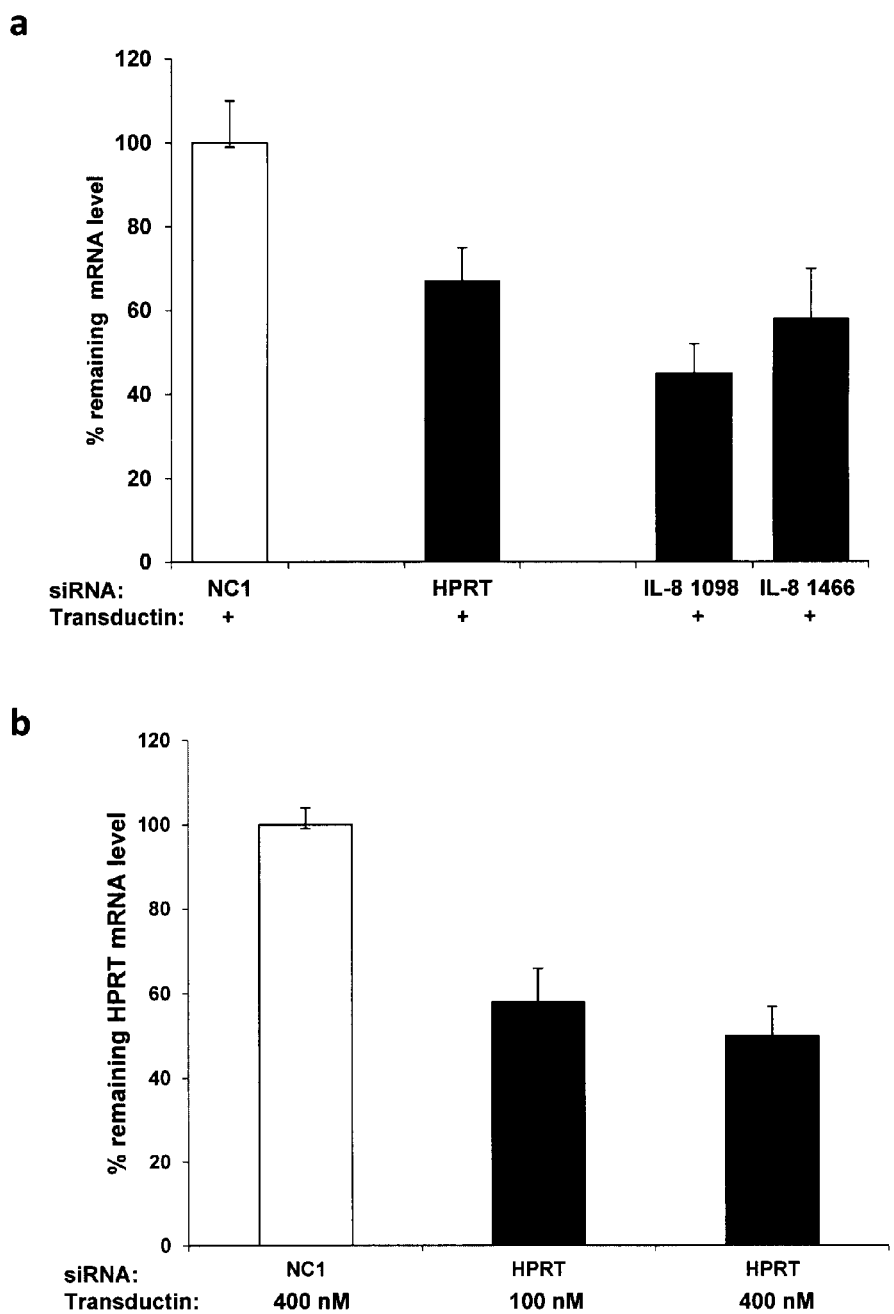

FIG. 9. siRNAs effectively silence targets in poorly differentiated cultures. (a) Knockdown of IL-8 is seen in poorly differentiated pig airway cultures upon transfection of either of the two siRNAs against IL-8 (1098 or 1466). siRNAs were transfected at a concentration of 250 ng. Twenty four hours later, qPCR was done to quantitate the mRNA levels in the samples and negative control. Knockdown of HPRT was also done as a control. (b) Silencing of HPRT is seen in poorly differentiated human airway epithelia when transfected using Transductin. Indicated amounts of HPRT siRNA was transfected into cells and 24 h later the samples were processed for qPCR. In both (a and b), sample mRNA levels were compared with that of negative control (100%). Mean levels (±s.d.) were calculated from three replicate transfections. Mean levels (±s.d.) were calculated from three replicate transfections.

Figure 10:
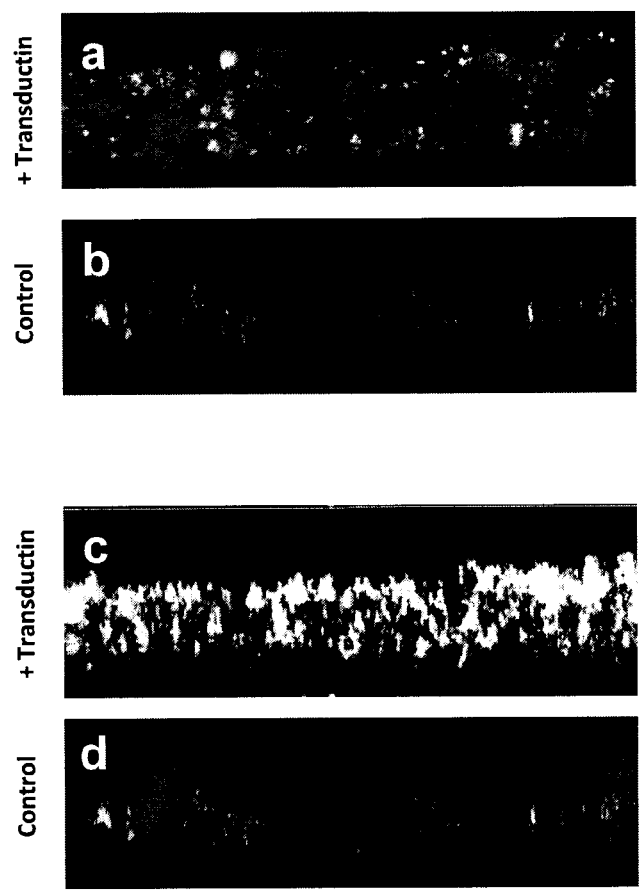

FIG. 10. Confocal imaging of human airway epithelial cells transfected with DIG-HPRT siRNA. (a-d) Human airway epithelia were transfected with 250 ng of DIG-HPRT siRNA after complexing it with Transductin. Two hours later the cells were processed for fluorescent imaging by confocal microscopy as detailed in Materials and Methods. (a-b) Imaging of well differentiated cells after transfection of DIG-HPRT siRNA with (a) or without (b) Transductin. (c-d) Imaging of poorly differentiated cells after transfection of DIG-HPRT siRNA with (c) or without (d) Transductin.

Figure 11:
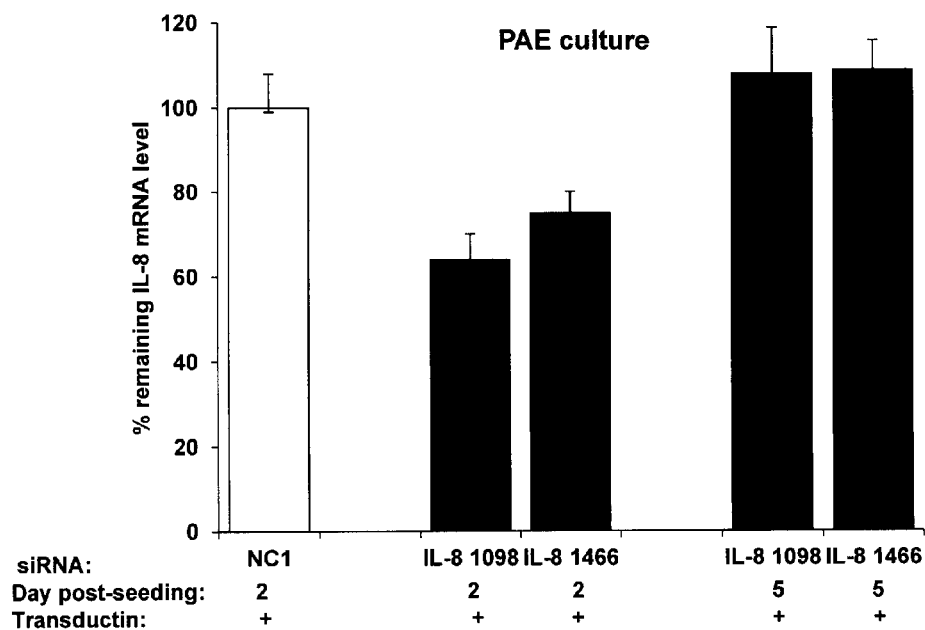
Figure 11:
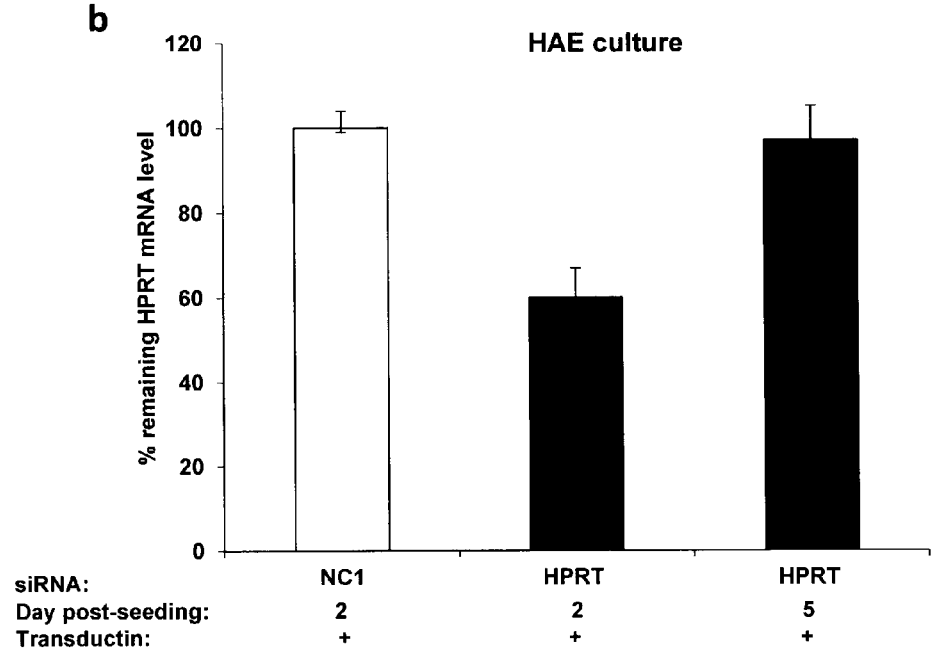

FIG. 11. Effective silencing of targets is seen only in cells that are less than 5-day old. (a) Silencing of IL-8 is seen in 2-day old pig airway epithelia, but not in 5-day old epithelia, when 250 ng of siRNA against IL-8 (1098 or 1466) is transfected into cells with Transductin. (b) In human airway epithelia, significant knockdown of HPRT is seen only in 2-day old cells, but not in 5-day old cells on transfection of 250 ng of siRNA against HPRT. In both experiments (a and b), quantification of mRNA levels were done by qPCR 24 h later and the results of the mRNA levels in samples are presented in comparison with those of the negative control (100%). Mean levels (±s.d.) were calculated from three replicate transfections.

Figure 12:
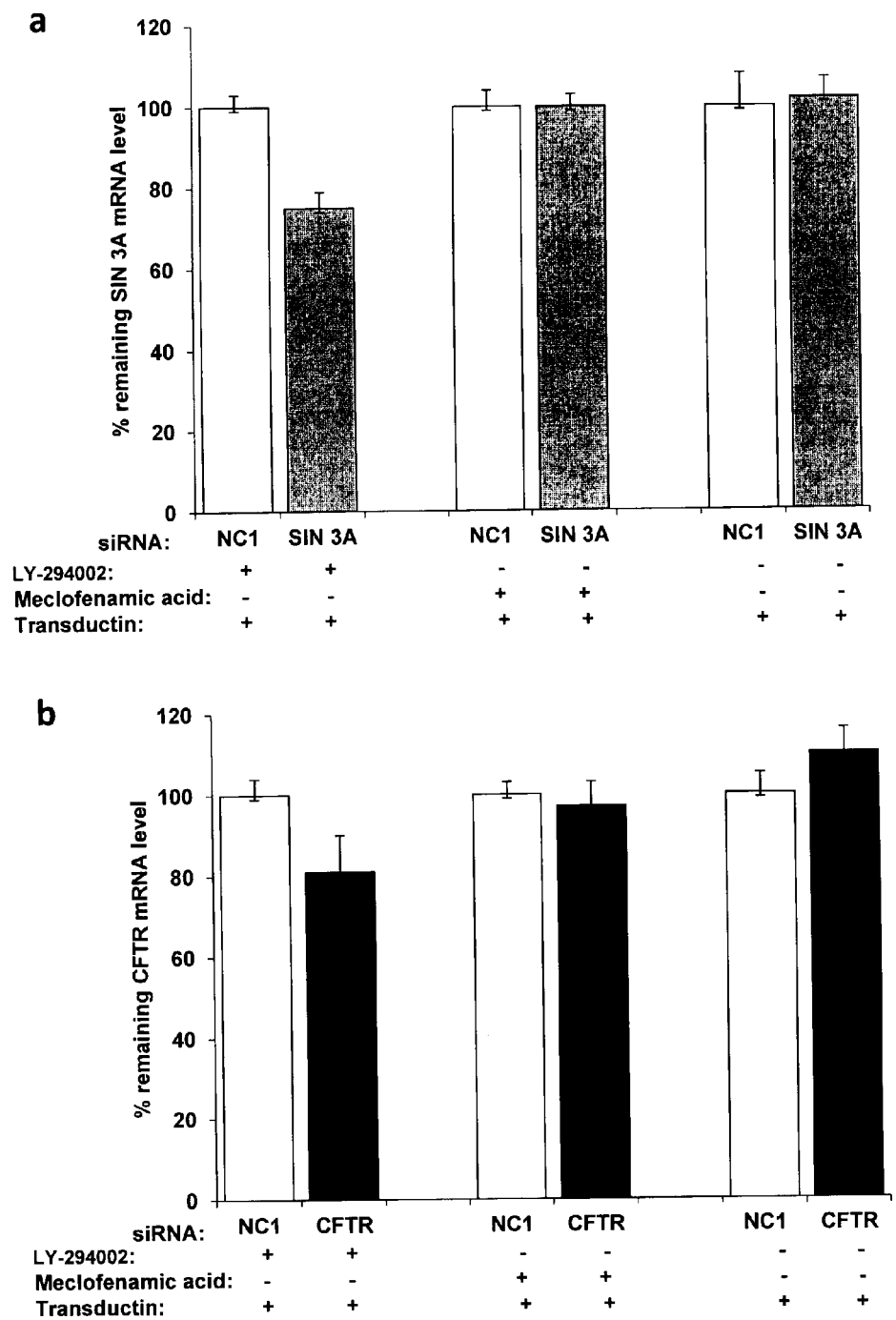

FIG. 12. Small molecule treatment of cells prior to siRNA delivery cause effective silencing of targets (a-b) LY-294002 treatment (10 µM) of human airway cells apically before transfection of siRNA causes knockdown of both Sin3A (a) and CFTR (b). The siRNA (concentration of 250 ng) was transfected with the use of Transductin and 24 h later the cells were harvested for RNA isolation and cDNA synthesis. The mRNA levels were quantified by qPCR and the results are presented as mRNA levels in comparison with that of the negative control (100%). Mean levels (±s.d.) were calculated from three replicate transfections.

DETAILED DESCRIPTION OF THE INVENTION

RNA interference (RNAi) is a powerful method to affect the abundance of a cellular protein. The delivery of RNAi oligonucleotides to airway epithelia has the potential to manipulate gene expression for therapeutic ends, and may be useful for diseases such as asthma, chronic obstructive pulmonary disease (COPD), and cystic fibrosis. However, inefficient delivery of reagents to target cells has hampered this line of therapeutic investigation.

It has been found that once airway epithelial cells become well differentiated, their barrier properties remarkably inhibit the uptake of RNAi oligonucleotides delivered to the mucosal surface of the cells in a variety of different formulations. The gene expression profiles of poorly differentiated and well differentiated human airway epithelial cells were profiled using the Connectivity map to discover classes of compounds that might enhance uptake of RNAi oligonucleotides. The treatment of well differentiated airway epithelia by applying with certain classes of drugs increased the uptake of RNAi oligonucleotides, and effected genes silencing. This approach is used to enhance the delivery of therapeutic oligonucleotides to the airways.

A large number of siRNA formulation approaches (lipid, cholesterol, TAT, chitosan formulations, etc.) have been screened, all showing no significant delivery or efficacy in well differentiated human or pig airway epithelia. In contrast, when the same formulations were tried on poorly differentiated cells (1-4 days in culture), the oligonucleotides were capable of being delivered, and attained mRNA knockdown. The current studies show that pretreatment of the mucosal surface of epithelia with EGF (200 µg/ml), enhanced uptake and facilitated siRNA knockdown in well differentiated cells. EGF can stimulate macropinocytosis in cells in a dose and cell type specific fashion. The present data establishes a principle whereby augmentation of macropinocytosis is manipulated to enhance oligonucleotide delivery.

In certain embodiments, the present invention provides methods of reducing a level of a target mRNA in a well-differentiated PAE cell comprising contacting the cell with a sensitizing agent followed by contacting the cell with a therapeutic RNAi agent, wherein the mRNA level of the target mRNA is reduced by at least 1% as compared to a control cell that has not been contacted with the sensitizing compound.

Sensitizing Agents

The inventors identified candidate chemical agents might be useful in sensitizing well differentiated airway epithelial cells to RNAi silencing. These candidate agents included LY-294003 (2-morpholin-4-yl-8-phenylchromen-4-one), wortmannin and triciribine. In certain embodiments, pharmaceutically acceptable salts of these compounds are used. For in vivo use, a therapeutic compound as described herein is generally incorporated into a pharmaceutical composition prior to administration. Within such compositions, one or more therapeutic compounds as described herein are present as active ingredient(s) (i.e., are present at levels sufficient to provide a statistically significant effect on the symptoms of cystic fibrosis, as measured using a representative assay). A pharmaceutical composition comprises one or more such compounds in combination with any pharmaceutically acceptable carrier(s) known to those skilled in the art to be suitable for the particular mode of administration. In addition, other pharmaceutically active ingredients (including other therapeutic agents) may, but need not, be present within the composition.

RNA Interference (RNAi) Molecules

"RNA interference (RNAi)" is the process of sequence-specific, post-transcriptional gene silencing initiated by a small interfering RNA (siRNA). During RNAi, siRNA induces degradation of target mRNA with consequent sequence-specific inhibition of gene expression.

An "RNA interference," "RNAi," "small interfering RNA" or "short interfering RNA" or "siRNA" or "short hairpin RNA" or "shRNA" molecule, or "miRNA" is a RNA duplex of nucleotides that is targeted to a nucleic acid sequence of interest, for example, SIN3A. As used herein, the term "siRNA" is a generic term that encompasses all possible RNAi triggers. An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In certain embodiments, the siRNAs are targeted to the sequence encoding SIN3A. In some embodiments, the length of the duplex of siRNAs is less than 30 base pairs. In some embodiments, the duplex can be 32, 31, 30, 29, 28, 27, 26, 25, 24, 23, 22, 21, 20, 19, 18, 17, 16, 15, 14, 13, 12, 11 or 10 base pairs in length. In some embodiments, the length of the duplex is 19 to 32 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24, 25, 26 or 27 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

As used herein, Dicer-substrate RNAs (DsiRNAs) are chemically synthesized asymmetric 25-mer/27-mer duplex RNAs that have increased potency in RNA interference compared to traditional siRNAs. Traditional 21-mer siRNAs are designed to mimic Dicer products and therefore bypass interaction with the enzyme Dicer. Dicer has been recently shown to be a component of RISC and involved with entry of the siRNA duplex into RISC. Dicer-substrate siRNAs are designed to be optimally processed by Dicer and show increased potency by engaging this natural processing pathway. Using this approach, sustained knockdown has been regularly achieved using sub-nanomolar concentrations. (U.S. Pat. No. 8,084,599; Kim et al., Nature Biotechnology 23:222 2005; Rose et al., Nucleic Acids Res., 33:4140 2005).

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional siRNAs. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional miRNAs or siRNAs. "Artificial miRNA" or an "artificial miRNA shuttle vector", as used herein interchangeably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (~35 nucleotides upstream and ~40 nucleotides downstream) arise from restriction enzyme sites within the multiple cloning site of the siRNA. As used herein the term "miRNA" encompasses both the naturally occurring miRNA sequences as well as artificially generated miRNA shuttle vectors.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

"Off-target toxicity" refers to deleterious, undesirable, or unintended phenotypic changes of a host cell that expresses or contains a siRNA. Off-target toxicity may result in loss of desirable function, gain of non-desirable function, or even death at the cellular or organismal level. Off-target toxicity may occur immediately upon expression of the siRNA or may occur gradually over time. Off-target toxicity may occur as a direct result of the expression siRNA or may occur as a result of induction of host immune response to the cell expressing the siRNA. Without wishing to be bound by theory, off-target toxicity is postulated to arise from high levels or overabundance of RNAi substrates within the cell. These overabundant or overexpressed RNAi substrates, including without limitation pre- or pri RNAi substrates as well as overabundant mature antisense-RNAs, may compete for endogenous RNAi machinery, thus disrupting natural miRNA biogenesis and function. Off-target toxicity may also arise from an increased likelihood of silencing of unintended mRNAs (i.e., off-target) due to partial complementarity of the sequence. Off target toxicity may also occur from improper strand biasing of a non-guide region such that there is preferential loading of the non-guide region over the targeted or guide region of the RNAi. Off-target toxicity may also arise from stimulation of cellular responses to dsRNAs which include dsRNA. "Decreased off target toxicity" refers to a decrease, reduction, abrogation or attenuation in off target toxicity such that the therapeutic effect is more beneficial to the host than the toxicity is limiting or detrimental as measured by an improved duration or quality of life or an improved sign or symptom of a disease or condition being targeted by the siRNA. "Limited off target toxicity" or "low off target toxicity" refer to unintended undesirable phenotypic changes to a cell or organism, whether detectable or not, that does not preclude or outweigh or limit the therapeutic benefit to the host treated with the siRNA and may be considered a "side effect" of the therapy. Decreased or limited off target toxicity may be determined or inferred by comparing the in vitro analysis such as Northern blot or qPCR for the levels of siRNA substrates or the in vivo effects comparing an equivalent shRNA vector to the miRNA shuttle vector of the present invention.

"Knock-down," "knock-down technology" refers to a technique of gene silencing in which the expression of a target gene is reduced as compared to the gene expression prior to the introduction of the siRNA, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of protein may be reduced by 10, 20, 30, 40, 50, 60, 70, 80, 90, 95, or 99%. In some embodiments, the expression is reduced by about 90% (i.e., only about 10% of the amount of protein is observed a cell as compared to a cell where siRNA molecules have not been administered). Knock-down of gene expression can be directed by the use of RNAi molecules.

In one embodiment according to a method of the present invention, the expression of cystic fibrosis is modified via RNAi. For example, SIN3A expression and/or function is suppressed in a cell. The term "suppressing" refers to the diminution, reduction or elimination in the number or amount of transcripts present in a particular cell. It also relates to reductions in functional protein levels by inhibition of protein translation, which do not necessarily correlate with reductions in mRNA levels. For example, the accumulation of mRNA encoding SIN3A is suppressed in a cell by RNA interference (RNAi), e.g., the gene is silenced by sequence-specific double-stranded RNA (dsRNA), which is also called small interfering RNA (siRNA). These siRNAs can be two separate RNA molecules that have hybridized together, or they may be a single hairpin wherein two portions of a RNA molecule have hybridized together to form a duplex.

A mutant protein refers to the protein encoded by a gene having a mutation, e.g., a missense or nonsense mutation in one or both alleles of a gene, such as CFTR, causing disease. The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters. An "allele" is one of several alternative forms of a gene occupying a given locus on a chromosome.

The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

A "nucleotide sequence" is a polymer of DNA or RNA that can be single-stranded or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid nucleic acid molecules and compositions containing those molecules. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

The terms "protein," "peptide" and "polypeptide" are used interchangeably herein.

"Functional RNA" refers to sense RNA, antisense RNA, ribozyme RNA, siRNA, or other RNA that may not be translated but yet has an effect on at least one cellular process.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

The siRNAs of the present invention can be generated by any method known to the art, for example, by in vitro transcription, recombinantly, or by synthetic means. In one example, the siRNAs can be generated in vitro by using a recombinant enzyme, such as T7 RNA polymerase, and DNA oligonucleotide templates.

Administration of Sensitizing and Therapeutic Agents

The sensitizing agent and therapeutic agent are administered to the patient so that the sensitizing and therapeutic agents contact cells of the patient's respiratory or digestive system. For example, the sensitizing and/or therapeutic agent may be administered directly via an airway to cells of the patient's respiratory system. The sensitizing and therapeutic agents can be administered intranasally (e.g., nose drops) or by inhalation via the respiratory system, such as by propellant based metered dose inhalers or dry powders inhalation devices.

Formulations suitable for administration include liquid solutions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. The therapeutic agent can be administered in a physiologically acceptable diluent in a pharmaceutically acceptable carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

The sensitizing and therapeutic agents, alone or in combination with other suitable components, can be made into aerosol formulations to be administered via inhalation. These aerosol formulations can be placed into pressurized acceptable propellants, such as dichlorodifluoromethane, propane, and nitrogen. Such aerosol formulations may be administered by metered dose inhalers. They also may be formulated as pharmaceuticals for non-pressured preparations, such as in a nebulizer or an atomizer. In certain embodiments, administration may be, e.g., aerosol, instillation, intratracheal, intrabronchial or bronchoscopic deposition.

In certain embodiments, the therapeutic agent may be administered in a pharmaceutical composition. Such pharmaceutical compositions may also comprise a pharmaceutically acceptable carrier and other ingredients known in the art. The pharmaceutically acceptable carriers described herein, including, but not limited to, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices. Viscoelastic gel formulations with, e.g., methylcellulose and/or carboxymethylcellulose may be beneficial (see Sinn et al., *Am J Respir Cell Mol Biol*, 32(5), 404-410 (2005)).

The sensitizing and therapeutic agents can be administered by any conventional method available for use in conjunction with pharmaceuticals, either as individual therapeutic agents or in combination with at least one additional therapeutic agent.

In certain embodiments, the sensitizing and therapeutic agents are administered with an agent that disrupts, e.g., transiently disrupts, tight junctions, such as EGTA (see U.S. Pat. No. 6,855,549).

The total amount of the sensitizing and therapeutic agents administered will also be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

The sensitizing and therapeutic agents can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The sensitizing and therapeutic agents may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the therapeutic agent can be determined by comparing their in vitro activity, and in vivo activity in animal models. Methods for the extrapolation of effective dosages in mice, and other animals, to humans are known to the art; for example, see U.S. Pat. No. 4,938,949.

The amount of the sensitizing and therapeutic agents, or an active salt or derivative thereof, required for use in treatment will vary not only with the particular salt selected but also with the route of administration, the nature of the condition being treated and the age and condition of the patient and will be ultimately at the discretion of the attendant physician or clinician.

Pharmaceutical compositions are administered in an amount, and with a frequency, that is effective to inhibit or alleviate the symptoms of airway epithelial disease (e.g., cystic fibrosis) and/or to delay the progression of the disease. The effect of a treatment may be clinically determined by nasal potential difference measurements as described herein. The precise dosage and duration of treatment may be determined empirically using known testing protocols or by testing the compositions in model systems known in the art and extrapolating therefrom. Dosages may also vary with the severity of the disease. A pharmaceutical composition is generally formulated and administered to exert a therapeutically useful effect while minimizing undesirable side effects. In general, an oral dose ranges from about 200 mg to about 1000 mg, which may be administered 1 to 3 times per day. Compositions administered as an aerosol are generally designed to provide a final concentration of about 10 to 50 µM at the airway surface, and may be administered 1 to 3 times per day. It will be apparent that, for any particular subject, specific dosage regimens may be adjusted over time according to the individual need. In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful to treat cystic fibrosis. Examples of such agents include antibiotics. Accordingly, in one embodiment the invention also provides a composition comprising a therapeutic agent, or a pharmaceutically acceptable salt thereof, at least one other therapeutic agent, and a pharmaceutically acceptable diluent or carrier. The invention also provides a kit comprising a therapeutic agent, or a pharmaceutically acceptable salt thereof, at least one other therapeutic agent, packaging material, and instructions for administering the therapeutic agent or the pharmaceutically acceptable salt thereof and the other therapeutic agent or agents to an animal to treat cystic fibrosis.

A pharmaceutical composition may be prepared with carriers that protect active ingredients against rapid elimination from the body, such as time release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

In certain embodiments, the sensitizing and therapeutic agents are directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of a variety of cosolvents, surfactants, stabilizers (e.g., antioxidants, chelating agents, inert gases and buffers). For compositions to be administered from multiple dose containers, antimicrobial agents are typically added. Such compositions are also generally filtered and sterilized, and may be lyophilized to provide enhanced stability and to improve solubility.

As noted above, sensitizing and therapeutic agents may be administered to a mammal to stimulate chloride transport, and to treat cystic fibrosis. Patients that may benefit from administration of a therapeutic compound as described herein are those afflicted with cystic fibrosis. Such patients may be identified based on standard criteria that are well known in the art, including the presence of abnormally high salt concentrations in the sweat test, the presence of high nasal potentials, or the presence of a cystic fibrosis-associated mutation. Activation of chloride transport may also be beneficial in other diseases that show abnormally high mucus accumulation in the airways, such as asthma and chronic bronchitis. Similarly, intestinal constipation may benefit from activation of chloride transport by the therapeutic agents provided herein.

The term "therapeutically effective amount," in reference to treating a disease state/condition, refers to an amount of a compound either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The terms "treat," "treating" and "treatment" as used herein include administering a compound prior to the onset of clinical symptoms of a disease state/condition so as to prevent any symptom, as well as administering a compound after the onset of clinical symptoms of a disease state/condition so as to reduce or eliminate any symptom, aspect or characteristic of the disease state/condition. Such treating need not be absolute to be useful.

Example 1

Airway Epithelia Requires Manipulation to Efficiently Internalize siRNA and Silence Target Genes The application of RNA interference-based gene silencing to the airway surface epithelium holds great promise to manipulate host and pathogen gene expression for therapeutic purposes. However, well-differentiated airway epithelia display significant barriers to double-stranded siRNA oligonucleotide ("oligo") delivery despite testing varied classes of non-viral reagents. In well-differentiated primary pig or human airway epithelia grown at air-liquid interface, the delivery of a Dicer-substrate siRNA duplex against HPRT with several non-viral reagents showed minimal oligo uptake and no knockdown of the target. In contrast, poorly differentiated cells (2-5 day post seeding) exhibited significant internalization of the oligo and knockdown of the target. This finding suggested that during differentiation the barrier properties of the epithelium are modified to an extent that impedes oligo uptake. Two methods were used to overcome this inefficiency. First, the impact of agents that enhance macropinocytosis were tested. Treatment of the cells with EGF, which induces actin polymerization and membrane protrusion, improved oligo uptake resulting in significant but modest levels of target knockdown. The connectivity map was also used to correlate gene expression signatures associated with mucociliary differentiation of airway epithelia with small molecule treatments. The resulting drugs identified were tested for their abilities to safely improve target knockdown. Interestingly, treatment of well-differentiated cells with several different drug classes resulted in modest to robust knockdown of the target when delivered along with a DsiRNA oligo. These results support that well-differentiated airway epithelia, normally resistant to siRNA delivery, when pretreated with small molecules, improved oligo uptake and RNAi responses.

This study explored the effectiveness of non-viral based siRNA delivery to reduce target abundance in well-differentiated primary airway epithelial cells. The results show that cells that are well-differentiated epithelia are almost completely refractory to entry of siRNA unless subjected to certain modifications.

Materials and Methods

Culture of Human or Pig Airway Epithelia

Pig airway epithelial cells were obtained from trachea of lungs removed from slaughtered pigs. The studies were approved by the institutional review board at the University of Iowa. Human airway epithelial cells were obtained from trachea and bronchi of lungs removed for organ donation from non-CF individuals. The studies were approved by the institutional review board at the University of Iowa. Cells were isolated by enzyme digestion as previously described (Karp P H et al., An in vitro model of differentiated human airway epithelia. Methods for establishing primary cultures. *Methods Mol Biol* 2002; 188:115-137). Following enzymatic dispersion, cells were seeded at a density of $5 \times 10^5$ cells/cm$^2$ onto collagen-coated, 0.6 cm$^2$ semi permeable membrane filters (Millipore polycarbonate filters; Millipore Corp., Bedford, Mass.). The cells were maintained at 37° C. in a humidified atmosphere of 5% $CO_2$ air. Twenty-four hours after plating, the apical media was removed and the cells were maintained at an air-liquid interface (ALI) to allow differentiation of the epithelium. The culture medium consisted of 1:1 ratio mix of Dulbecco's modified Eagle's medium (DMEM)/Ham's F12, 5% Ultroser G (Biosepra SA, Cedex, France), 100 U/ml penicillin, 100 μg/ml streptomycin, 1% nonessential amino acids and 0.12 U/ml insulin. Studies were performed on WD cultures confirmed as cultures containing ciliated cells (by confocal microscopy) approximately 4 to 6 weeks after initiation of the ALI cultures.

Dicer-Substrate siRNA Oligonucleotides

The 27-mer Dicer-substrate siRNAs (DsiRNAs) were designed using algorithms developed by Integrated DNA Technologies (IDT, Coralville, Iowa) and synthesized and HPLC purified by IDT. The protocol for siRNA design and manufacture has been described in detail (Kim D H et al., Synthetic dsRNA dicer substrates enhance RNAi potency and efficacy. *Nat Biotechnol* 2005; 23(2):222-226; Behlke M A. Chemical modification of siRNAs for in vivo use. *Oligonucleotides* 2008; 18(4):305-319). The digoxigenin (Dig)-labeled siRNA was also designed and synthesized by IDT. The DIG label was internally coupled to an amino-dT base in a 2-O' methyl modified pig-specific DsiRNA against HPRT. The DsiRNAs used in this study are listed in Table 1.

TABLE 1

Dicer-substrate siRNA

| siRNA | Target mRNA | siRNA target sequence | |
|---|---|---|---|
| ssHPRT | Pig HPRT | 5'  pCCAGUAAAGUUAUCACAUGUUCUAG | SEQ ID NO: 1 |
|  |  | 3'  GGIGUCAUUUCAAUAGUGUACAAGAUC | SEQ ID NO: 2 |

TABLE 1-continued

Dicer-substrate siRNA

| siRNA | Target mRNA | siRNA target sequence | | |
|---|---|---|---|---|
| hsHPRT | Human HPRT | 5' pGCCAGACUUUGUUGGAUUUGAAATT | SEQ ID NO: | 3 |
| | | 3' UUCGGUCUGAAACAACCUAAACUUUAA | SEQ ID NO: | 4 |
| IL-8 1098 | Pig IL-8 | 5' pGGCAAAUUGUUAAACGAACAGAATA | SEQ ID NO: | 5 |
| | | 3' AACCGUUUAACAAUUUGCUUGUCUUAU | SEQ ID NO: | 6 |
| IL-8 1466 | Pig IL-8 | 5' pUGAGUGUAACUAUAGAACAUUUACA | SEQ ID NO: | 7 |
| | | 3' ACACUCACAUUGAUAUCUUGUAAAUGU | SEQ ID NO: | 8 |
| SIN3A | Human SIN3A | 5' pGCGAUACAUGAAUUCAGAUACUACC | SEQ ID NO: | 9 |
| | | 3' <u>CUCGCU</u>AUGUACUU<u>AA</u>GUCUAUGAUGG | SEQ ID NO: | 10 |
| CFTR | Human CFTR | 5' pGGAAGAAUUCUAUUCUCAAUCCAT | SEQ ID NO: | 11 |
| | | 3' <u>UUCCUUCU</u>UAAGAU<u>AA</u>GAGUUAGGUUA | SEQ ID NO: | 12 |
| DIG-HPRT | Pig HPRT | 5' pCCAGUAAAGUUA*T*CACAUGUUCUAG | SEQ ID NO: | 13 |
| | | 3' G<u>UGGU</u>CAUUUCAAUA<u>G</u>UGUACAAGA<u>UC</u> | SEQ ID NO: | 14 |
| NC1 | No known targets in pig or human | 5' pCGUUAAUCGCGUAUAAUACGCGUAT | SEQ ID NO: | 15 |
| | | 3' CAGCAAUUAGCGCAUAUUAUGCGCAUA | SEQ ID NO: | 16 |

DNA bases are in bold; 2 O'methyl bases are underlined; amino dT base coupled to DIG is in italics Non-Viral Reagents RNAiMAX was purchased from Invitrogen (Invitrogen, Grand Island, N.Y.). The cationic polymers, PEI, and TAT-PEI were synthesized and conjugated with siRNA into appropriate NP concentration in the laboratory of Dr. Aliasger Salem at University of Iowa. Accell siRNA (Thermo Scientific, Lafayette, Colo.), the naked siRNA chemically modified for increased functionality, stability and enhanced uptake by cells, was custom synthesized as 21-nt siRNA with a sequence for control NC1 and a sequence against pig HPRT. PTD-DRBD was purchased as Transductin from IDT (IDT, Coralville, Iowa).

Transfection

For airway epithelia that were either well or poorly differentiated, transfection was done mostly according to the manufacturer's protocol. In all cases, the apical surface of epithelia was washed twice with PBS before adding the transfection mixture to the apical surface. The mixture was then left on the cells for 24 h for all transfection reagents. For PK1 cells, reverse transfection was performed in a 48-well plate by first adding the siRNA-RNAiMAX reagent mixture onto the plate and then adding the dispersed cells (40,000 cells) on top of the mixture and allowing the cells to adhere and establish growth for 24 h. Before some transfections, pretreatment of cells with various chemicals were performed: Keratinocyte Growth Factor (KGF; Prospec, East Brunswick, N.J.) 50 ng/ml added both apically and basolaterally for 24 h; EGTA 6 mM added apically for 30 m; N-Acetyl-L-Leucyl-L-Leucyl-L-Norleucinal (LLnL; ICN Biochemicals, Inc, Costa Mesa, Calif.) 40 μM added both apically and basolaterally for 24 hrs; human Epidermal Growth Factor (EGF; Sigma-Aldrich, St. Louis, Mo.) 100 μg/ml, added apically for 15 m.

RNA Isolation and Quantitative Real-Time PCR

Total RNA was isolated using SV96 RNA isolation kit (Promega), according to manufacturer's protocol. Two hundred fifty ng of total RNA were reverse transcribed using oligo (dT) (Roche, Indianapolis, Ind.) and random hexamers (Invitrogen, Grand Island, N.Y.) and Superscript II (Invitrogen, Grand Island, N.Y.) according to manufacturer's instructions. One-fifteenth of the cDNA was then amplified and analyzed by Taqman assay in the 7900 Real Time PCR System (Applied Biosystems) using synthesized primer-probe pairs (IDT, Coralville, Iowa), reaction buffer and Immolase DNA polymerase (Bioline, Taunton, Mass.). The reaction mix was contained in a total volume of 10 μl and the reaction condition was an initial cycle of 95° C. for 10 min, then 40 cycles of 95° C. for 15 s and 60° C. for 1 min. All data were normalized to the internal standard, RPL4 mRNA for pig airway samples and SFRS9 mRNA for human airway samples. Absolute quantification of an mRNA target sequence within an unknown sample was determined by reference to a standard curve. The standard curve was based on the real-time PCR amplification of standard amounts of the specific gene in a control NC1 cDNA. PCR efficiency for all reactions was within the acceptable margin of 90-110%. All the results of the samples were presented as remaining mRNA level in comparison to the mRNA level in the control samples (NC1), which was normalized to 100%.

Confocal Imaging

The primary human airway epithelia grown at air-liquid interface were transfected with the DIG-labeled siRNA at a concentration of 250 ng/ml after complexing with Transductin. The transfection mixture was left on the apical surface for 2 h. At the end of this period, the cells were fixed in 2% formaldehyde, permeabilized in 0.2% Triton-x-100 and blocked in 1% BSA for 1 h. The cells were then stained with mouse antibody to DIG (Roche Biochemicals) for 1 h followed by either Alexa 488 labeled goat anti-mouse secondary antibody for 1 h followed by Alexa 488 labeled rabbit anti-mouse tertiary antibody (Invitrogen) for 1 or in some cases with Alexa 564 goat anti-mouse secondary antibody for 1 h. The cells were finally stained with nuclear stain, ToPro 3 for 10 minutes. The filter, containing the cells, was removed from the culture insert by cutting the edges with razor blade and then mounted onto a slide by the use of Vectashield. The slide was visualized by confocal microscopy.

Connectivity Map Analysis

The connectivity map is a large public database (Lamb J et al., The connectivity map: Using gene-expression signatures to connect small molecules, genes, and disease. *Science* 2006; 313(5795):1929-1935) of gene expression data sets in response to drug treatments that can be used to connect a researcher's gene expression signatures, explaining a particular biological process, with small molecules that share a similar mechanism of action. The input query signature in our study was a published microarray profile (Ross A J et al., Transcriptional profiling of mucociliary differentiation in human airway epithelial cells. *Am J Respir Cell Mol Biol* 2007; 37(2):169-185) that reflects the longitudinal gene expression changes associated with mucocilliary differentiation of the human bronchial epithelial cells. Specifically, genes that had more than 3-fold expression changes during the differentiation of cells from 0-day old cultures to 4-day old cultures or 0 day cultures to 8-day old cultures or 4-day old cultures to 8-day old cultures were used as input signatures (probe ID defined by the Affymetrix GeneChip Human Genome U133A array). Each reference signature in the database was compared with the input signature and given a score termed the "connectivity score" based on the extent of similarity between the two. Score ranged from +1 meaning higher similarity, to 0 meaning no similarity and −1 meaning opposite similarity. We evaluated candidate agents that induced a 'reverse signature' (connectivity score of −1 or closer to it), i.e. changes in gene expression in a direction opposite to the differentiation process. Also, some were selected from the permuted results, which give statistical significance of the replicates (permutation P value).

Small Molecules

Wortmannin was purchased from Sigma (St. Louis, Mo.) as a ready to use solution. LY-294002, Triciribine hydrate, and Meclofenamic acid were purchased from Sigma (St. Louis, Mo.) and were dissolved in DMSO. Monensin was purchased from Sigma (St. Louis, Mo.) and was dissolved in water. For experiments with drugs, the cells were pre-treated with drugs for 6 h usually at a concentration that was used in the Cmap study (Lamb J et al., The connectivity map: Using gene-expression signatures to connect small molecules, genes, and disease. *Science* 2006; 313(5795):1929-1935) or in other published studies. After the drug treatment, the cells were transfected with siRNA as described before.

Results

Dicer-Substrate siRNA Silence Gene Expression in PK1 Cells siRNAs were designed and synthesized to specifically target pig HPRT (ssHPRT) and IL-8 (IL-8 1098 and IL-8 1466). The efficacy and the functionality of these siRNAs were tested by reverse transfecting them into a pig kidney cell line (PK1). Quantitative real-time PCR was performed to measure the extent of mRNA reduction. FIG. 1 shows the remaining mRNA levels of the respective genes 24 h post translation. A nontargeting siRNA was used as a control (NC1). The targeting mRNA was decreased by more than 90% when the cells were treated with two different concentrations (1 nM and 10 nM) of specific siRNAs as compared with the nontargeting control (FIG. 6). The siRNAs targeting the human genes (HPRT, SIN3A and CFTR) were either tested directly in primary airway cultures maintained in air-liquid interface, or tested in other cell lines (data not shown). The sequences of all the siRNAs are listed (see Table 1).

siRNA delivery has no silencing effect in well differentiated cultures

The goal was to test the effectiveness of the siRNA in primary airway epithelial cells. Well differentiated airway cultures are maintained at the air-liquid interface and simulate to a great extent the in vivo morphology and thus are an ideal system to test efficacy of siRNA and nonviral delivery reagents. Various nonviral reagents or siRNA enhancements were tested, including cationic polymers (PEI or TAT-PEI), modified naked siRNA (Accell), peptide reagent (PTD-DRBD or Transductin) and lipid transfection reagent (RNAiMAX) in well-differentiated cells. As shown in FIG. 2, no silencing of HPRT mRNA was observed on apical transfection of HPRT siRNA into pig airway cells with polymers, Accell or Transductin (FIG. 1*a*). Nor was there a reduction of HPRT mRNA levels in human airway epithelia following transfection of siRNA conjugated with RNAiMAX or Transductin (FIG. 7). Thus, well-differentiated airway cultures are not amenable to siRNA transfection with a broad range of transfection reagents and siRNA targets were not inhibited.

Well-Differentiated Transfected Cells on Imaging Show Minimal Uptake of siRNA

After failing to silence targets in well-differentiated cells, it was investigated if the reason for this failure was because of a failure to uptake siRNA. siRNA was labelled with DIG and transfected them into cells using Transductin. Subsequently, the cell layers were fixed and processed for detection of the DIG label using fluorescent labeled anti-DIG antibodies. Confocal imaging of the cells revealed little to no internalization of siRNA in both pig airway cells (FIG. 1*b,c*) and human airway cells (FIG. 10*a, b*). The results suggest that the inability of the epithelia to silence gene expression is largely due to a failure of the siRNA to enter the cells.

KGF, EGTA, and LLnL Treatment of Cells Prior to siRNA Treatment have No Effect on Target Silencing The decreased ability of well-differentiated cells to uptake siRNA prompted the inventors to investigate the effect of interventions known to influence cellular processes including proliferation, permeability, processing on siRNA transfection and silencing. Keratinocyte growth factor (KGF) is a member of the fibroblast growth factor family. It has been shown previously that KGF stimulates proliferation of differentiated human tracheal and bronchial epithelia. Pretreatment of pig airway cells with KGF prior to transfection of specific siRNA with either RNAiMAX or Transductin did not reduce the mRNA levels of HPRT in comparison to nonsilencing siRNA (FIG. 8*a*). In addition, the cells were treated with EGTA, a calcium chelator, which causes a reversible increase in paracellular permeability. Similar to the result seen with KGF, siRNA transfection of cells with either RNAiMAX or Transductin, after treatment with EGTA, did not result in silencing of HPRT (FIG. 8*b*). Lastly, the cells were treated with a proteasome inhibitor (LLnL) prior to transfection. LLnL is a tripeptide proteasome inhibitor and has been shown to enhance recombinant adeno-associated virus type 2 (rAAV-2) transduction from the apical surface of human airway epithelia by modulating the intracellular trafficking and processing of the virus. We wanted to examine if LLnL has an effect on transfection efficiency and endocytosis of siRNA as well. Treatment with LLnL had no effect on silencing of HPRT following transfection of specific siRNA with either RNAiMAX or Transductin (FIG. 8*c*). Thus, well-differentiated cells are refractory to siRNA transfection even with certain physiological manipulation of the cells.

siRNA Delivery Effectively Silences Targets in Poorly Differentiated Epithelia

Since well-differentiated cells exhibit significant extracellular barriers to siRNA entry, it was hypothesized that poorly-differentiated cells, which lack many barriers of mature cells, might be conducive to siRNA entry and knockdown of the target gene. In contrast to well differentiated culture, poorly differentiated epithelia lack ciliated and goblet cells and do not have a pseudo stratified columnar architecture. On transfection of poorly differentiated pig airway epithelia (2-day old post seeding) with siRNA against HPRT, a decrease in mRNA levels was seen with all transfection reagents used. siRNA transfection showed decrease in HPRT mRNA levels of about 40% with RNAiMAX, 60-70% with Accell, and about 50%-60% with Transductin (FIG. 2). Similar reduction was also seen when these cells were transfected with siRNA against pig IL-8 (FIG. S4a) or poorly differentiated human airway cells were transfected with HPRT (Supplementary FIG. 9b). These results demonstrated that airway cells very early post seeding and hence not well differentiated are conducive to transfection of siRNA and knockdown of targets.

Poorly Differentiated Transfected Cells on Imaging Show Good Uptake of siRNA

After observing the silencing of target genes in poorly differentiated epithelia, it was examined whether siRNA internalization can be visualized as a result. Two days after seeding, cells were studied for siRNA uptake by transfecting the DIG-labeled siRNA with Transductin and subsequently imaging 2 h later by confocal microscopy. In contrast to results in well differentiated cells, abundant internalization of siRNA was observed in both pig and human airway epithelia (FIG. 2b,c and FIG. 10c,d). In combination with previous results, these data indicate that siRNAs can silence targets in poorly differentiated airway epithelia by virtue of their ability to readily enter these cells.

Effective Silencing of Targets are Seen Only in Cells that are Less than 5-Day Old The previous results showed that following siRNA transfection, silencing is seen in poorly differentiated (2-day post seeding), but not in well-differentiated epithelial cells. Next it was investigated how the time in culture after cell seeding influenced siRNA entry and target knockdown. Primary airway epithelia, maintained at air-liquid interface, take a minimum of two-four weeks after seeding to fully differentiate into a pseudo-stratified columnar epithelium. Cells obtained from two donors of pigs were seeded and batches of cells from 2 to 5 days post seeding were transfected with HPRT siRNA complexed with Transductin. Quantitative real time PCR was used to estimate the levels of mRNA remaining compared to those of nontargeting siRNA. As shown in FIG. 3a, in both donor cultures tested, 20-45% reduction in HPRT mRNA was seen in cultures of day 2 to day 4. In contrast, no silencing was seen in cells that were 5-days old (FIG. 3a). Alternatively, the cells were also visualized for siRNA entry after DIG-siRNA transfection following 2 to 5 days in culture. The presence or absence of knockdown of the target correlated with the internalization of DIG-siRNA (FIG. 3b-e). Cells transfected with siRNA against IL-8 also showed decrease in IL-8 mRNA in 2-day old cells, but not in 5-day old cells (FIG. 11a). Similarly, human airway epithelial showed no knockdown of HPRT in 5 day old cultures (FIG. 11b). Thus, silencing of targets is restricted to a narrow time window in culture before cells undergo differentiation.

EGF Treatment of Cell Prior to siRNA Delivery Enhances siRNA Entry and Cause Modest Silencing It can be concluded from the these results that during and after differentiation the barrier properties of the epithelia impede siRNA entry. It was hypothesized that manipulation of the cells to enhance endocytosis might promote better cellular uptake of siRNA and silencing of target genes. Epidermal Growth Factor (EGF) induces rapid actin filament assembly in the membrane skeleton of variety of cells, which can result in membrane ruffling and macropinocytosis. The inventors reasoned that since the Tat protein, the cell penetrating domain of Transductin, has been shown to enter cells through macropinocytosis, EGF treatment of cells prior to transfection of siRNA-Transductin complex might enhance cellular entry of siRNA. Human airway cells treated with EGF (100 µg/ml for 15 min) prior to transfection of siRNA showed decrease in HPRT mRNA levels of about 15-20% consistently when examined with cultures from 3 different donors (FIG. 4a). EGF treated cells (100 µg/ml for 15 min) imaged for siRNA entry 2 h after transfection showed increased uptake of the DIG signal compared to the untreated cells (data not shown). These results show that a transient cellular response to EGF can increase both the uptake of siRNA and silencing of target genes.

Connectivity Map Analysis Links Gene Signature of Mucociliary Differentiation to Small Molecules Ross et. al (Ross A J et al., Transcriptional profiling of mucociliary differentiation in human airway epithelial cells. *Am J Respir Cell Mol Biol* 2007; 37(2):169-185) previously identified genes involved in mucociliary differentiation of human bronchial epithelial cells grown at air-liquid interface over a period of 28-days. Since the results of our experiments show effective silencing of target genes in cells less than one week old, the gene expression profiles from cells at days, 0, 4 and 8 of culture was utilized. It was theorized that changes in gene expression during these periods might contribute to the development of barriers to siRNA entry. To identify small molecule agents that induce or counteract these changes, the connectivity map (Cmap) database was queried (Lamb J et al., The connectivity map: Using gene-expression signatures to connect small molecules, genes, and disease. *Science* 2006; 313(5795):1929-1935). Connectivity map is a large public database of gene expression in response to drug treatment of cell lines. Investigators compare a genomic signature describing physiological state or disease to the Cmap database to discover connections among drugs, genes and diseases. The database was queried using signatures comprised of >3-fold gene expression changes from epithelia between 0 and 4 days, 0 and 8 days and 4 and 8 days during mucociliary differentiation of airway culture. Several small molecular agents were positively or negatively correlated to the reference signatures. The inventors were interested in agents that might drive gene expression changes in well differentiated airway cells towards poorly differentiated cells and therefore had high negative or anti-correlation score with respect to reference signature. Four agents were selected that were highly ranked with a strong anti-correlation score (connectivity score of −1 or closer to −1). These included LY-294002, ergocalciferol, paclitaxel, and nifedipine. Two additional agents that were highly ranked in the permuted results according to their P-values were also selected: naltrexone and fasudil. As a negative control in the present experiments, two drugs were selected, monensin, and meclofenamic acid, that had strong positive correlation scores (connectivity score of +1 or closer to +1).

Small Molecule Treatment of Cells, Based on Connectivity Map, Prior to siRNA Delivery Cause Effective Silencing of Targets Primary airway epithelia were treated with the selected small molecular agents at a concentration that was selected from the Cmap study or published literature. The time of treatment was 6 hours as used in the Cmap study. At the end of 6 h, the cells were transfected with siRNA-Transductin complex for a period of 24 h before the cells were processed for qPCR to quantitate the mRNA levels in the samples. When the pig or human epithelia were transfected with the specific siRNA against HPRT, we observed no reduction in mRNA levels for treated with ergocalciferol, paclitaxel, nifedipine, naltrexone or fasudil (data not shown). In contrast, following LY-294002 treatment (10 µM), human and pig epithelia showed silencing of HPRT at a level of about 40% (FIG. 5a) and 20% (FIG. 5b) respectively, compared to that of nontargeting control. Results from several donor cells showed a range of silencing effects, 10-55% inhibition in human airway cells and 10-20% in pig airway cells (data not shown).

The siRNA silencing effect was a result of improved siRNA uptake, as shown by fluorescent images of cells treated with LY-294002 and transfected with DIG-siRNA (data not shown). LY-294002 inhibits all four classes of PI3K isoforms and has been one of the most successful and most widely used pathway inhibitors. The PI3K pathway, which is inhibited by LY-294002, is activated by upstream receptor tyrosine kinases by various growth factors. Activation of this pathway results in a broad range of downstream signaling events, mostly growth promoting or pleiotropic effects. Independent of its kinase inhibition mechanism of action, LY-294002 can also cause certain other effects in cells. In order to identify the enhanced silencing effect following LY-294002 treatment is a result of PI3K pathway inhibition or because of its other actions, cells were treated with other PI3K pathway inhibitors, namely wortmannin and triciribine. Wortmannin, unlike LY-294002, is an irreversible inhibitor of PI3K pathway and triciribine is an inhibitor of AKT, a downstream effector in the PI3K pathway. Since treatment of pig epithelia resulted in moderate decreases in mRNA levels, we decided to use only human airway cells for further experiments. Pretreatment of epithelia with increasing doses of wortmannin and triciribine before siRNA transfection resulted in dose dependent decreases in HPRT mRNA levels (FIG. 5c). Treatment of cells with 10 nM and 40 nM of wortmannin resulted about 20% and 30% decrease, respectively, in HPRT mRNA levels compared to that of nontargeting controls; while treatment of cells with 20 µM and 60 µM triciribine resulted in 20% and 35% decrease, respectively, in HPRT mRNA levels compared to that of nontargeting controls (FIG. 5c). These findings suggest that the improved silencing of siRNA target is a consequence of cellular changes that occur in response to PI3K pathway. The effects of LY-294002 were also tested on two other siRNA gene targets, namely CFTR and SIN3A. Pretreatment of human airway cells with 10 mM of LY-294002 before transfection with specific siRNA resulted in 20% and 25% reduction in mRNA levels of CFTR and SIN3A, respectively, when compared to that of nontargeting control (FIG. 12a,b).

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of reducing a level of a target mRNA in a well-differentiated airway epithelial cell comprising contacting the cell with an agent comprising a small molecule PI3K inhibitor, EGF, LY-294002, wortmannin or triciribine followed by contacting the cell with a therapeutic RNAi molecule, wherein the mRNA level of the target mRNA is reduced by at least 1% as compared to a control cell that has not been contacted with the agent.

2. The method of claim 1, wherein the mRNA level of the target mRNA is reduced by at least 10%.

3. The method of claim 1, wherein the mRNA level of the target mRNA is reduced by at least 20%.

4. The method of claim 1, wherein the RNAi molecule is an siRNA, an miRNA, and/or an anti-sense oligonucleotide.

5. The method of claim 1, wherein the cell is contacted on its mucosal surface.

6. The method of claim 1, wherein the airway epithelial cell is a lung cell, a nasal cell, a tracheal cell, a bronchial cell, a bronchiolar or alveolar epithelial cell.

7. A method of treating a subject having an airway epithelial disease comprising administering to the subject an effective amount of an agent comprising a small molecule PI3K inhibitor, EGF, LY-294002, wortmannin or triciribine and an effective amount of a therapeutic RNAi molecule.

8. The method of claim 7, wherein the agent is administered orally.

9. The method of claim 7, wherein the agent is administered by inhalation.

10. The method of claim 7, wherein the agent is administered by aerosol, dry powder, bronchoscopic instillation, or intra-airway (tracheal or bronchial) aerosol.

11. The method of claim 7, wherein the therapeutic RNAi molecule is administered orally, by inhalation, by aerosol, dry powder, bronchoscopic instillation, or intra-airway (tracheal or bronchial) aerosol.

12. The method of claim 7, wherein the airway epithelial disease is cystic fibrosis.

13. The method of claim 7, wherein the subject is a mammal.

14. The method of claim 13, wherein the subject is a human.

15. The method of claim 7, wherein the therapeutic RNAi molecule is present within a pharmaceutical composition.

* * * * *

SEQUENCE LISTING

```
<160> NUMBER OF SEQ ID NOS: 16

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Phosphorylated base

<400> SEQUENCE: 1
ccaguaaagu uaucacaugu ucuag                                           25

<210> SEQ ID NO 2
```

```
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(25)
<223> OTHER INFORMATION: Inosine

<400> SEQUENCE: 2
cuagaacaug ugauaacuuu acugngg                                        27

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Phosphorylated base

<400> SEQUENCE: 3
gccagacuuu guuggauuug aaatt                                          25

<210> SEQ ID NO 4
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
aauuucaaau ccaacaaagu cuggcuu                                        27

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Phosphorylated base

<400> SEQUENCE: 5
ggcaaauugu uaaacgaaca gaata                                          25

<210> SEQ ID NO 6
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
```
uauucuguuc guuuaacaau uugccaa         27

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Phosphorylated base

<400> SEQUENCE: 7
ugaguguaac uauagaacau uuaca         25

<210> SEQ ID NO 8
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uguaaauguu cuauaguuac acucaca         27

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Phosphorylated base

<400> SEQUENCE: 9
gcgauacaug aauucagaua cuacc         25

<210> SEQ ID NO 10
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 2 O'methyl base
<220> FEATURE:
<221> NAME/KEY: modified_base
<222> LOCATION: (13)..(13)
<223> OTHER INFORMATION: 2 O'methyl base
<220> FEATURE:
<221> NAME/KEY: modified_base
<222> LOCATION: (21)..(21)
<223> OTHER INFORMATION: 2 O'methyl base
<220> FEATURE:
<221> NAME/KEY: modified_base
<222> LOCATION: (23)..(23)
<223> OTHER INFORMATION: 2 O'methyl base -continued

```
<220> FEATURE:
<221> NAME/KEY: modified_base
<222> LOCATION: (25)..(27)
<223> OTHER INFORMATION: 2 O'methyl base

<400> SEQUENCE: 10
gguaguaucu gaauucaugu aucgcuc                                              27

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Phosphorylated base

<400> SEQUENCE: 11
ggaagaauuc uauucucaau ccaat                                                25

<210> SEQ ID NO 12
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 2 O'methyl base
<220> FEATURE:
<221> NAME/KEY: modified_base
<222> LOCATION: (13)..(13)
<223> OTHER INFORMATION: 2 O'methyl base
<220> FEATURE:
<221> NAME/KEY: modified_base
<222> LOCATION: (21)..(21)
<223> OTHER INFORMATION: 2 O'methyl base
<220> FEATURE:
<221> NAME/KEY: modified_base
<222> LOCATION: (23)..(23)
<223> OTHER INFORMATION: 2 O'methyl base
<220> FEATURE:
<221> NAME/KEY: modified_base
<222> LOCATION: (25)..(27)
<223> OTHER INFORMATION: 2 O'methyl base

<400> SEQUENCE: 12
auuggauuga gaauagaauu cuuccuu                                              27

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Phosphorylated base
<220> FEATURE:
<221> NAME/KEY: modified_base
```

```
<222> LOCATION: (1)..(2)
<223> OTHER INFORMATION: 2 O'methyl base
<220> FEATURE:
<221> NAME/KEY: misc_feature
<222> LOCATION: (13)..(13)
<223> OTHER INFORMATION: dT base coupled to DIG
<220> FEATURE:
<221> NAME/KEY: modified_base
<222> LOCATION: (24)..(24)
<223> OTHER INFORMATION: 2 O'methyl base

<400> SEQUENCE: 13
ccaguaaagu uatcacaugu ucuag                                         25

<210> SEQ ID NO 14
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2 O'methyl base
<220> FEATURE:
<221> NAME/KEY: modified_base
<222> LOCATION: (11)..(11)
<223> OTHER INFORMATION: 2 O'methyl base
<220> FEATURE:
<221> NAME/KEY: modified_base
<222> LOCATION: (13)..(13)
<223> OTHER INFORMATION: 2 O'methyl base
<220> FEATURE:
<221> NAME/KEY: modified_base
<222> LOCATION: (21)..(21)
<223> OTHER INFORMATION: 2 O'methyl base
<220> FEATURE:
<221> NAME/KEY: modified_base
<222> LOCATION: (23)..(23)
<223> OTHER INFORMATION: 2 O'methyl base
<220> FEATURE:
<221> NAME/KEY: modified_base
<222> LOCATION: (25)..(27)
<223> OTHER INFORMATION: 2 O'methyl base

<400> SEQUENCE: 14
cuagaacaug ugauaacuuu acuggug                                       27

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Phosphorylated base

<400> SEQUENCE: 15
cguuaaucgc guauaauacg cguat                                         25

<210> SEQ ID NO 16
<211> LENGTH: 27
<212> TYPE: RNA
<213> ORGANISM: Artificial Sequence
<220> FEATURE:
<223> OTHER INFORMATION: Description of Artificial Sequence: Synthetic
```

```
        oligonucleotide

<400> SEQUENCE: 16
auacgcguau uauacgcgau uaacgac                                                27
```